United States Patent
Anderson et al.

(10) Patent No.: US 7,041,481 B2
(45) Date of Patent: May 9, 2006

(54) CHEMICAL AMPLIFICATION BASED ON FLUID PARTITIONING

(75) Inventors: Brian L. Anderson, Lodi, CA (US); Billy W. Colston, Jr., San Ramon, CA (US); Chris Elkin, San Ramon, CA (US)

(73) Assignee: The Regents of the University of California, Oakland, CA (US)

(*) Notice: Subject to any disclaimer, the term of this patent is extended or adjusted under 35 U.S.C. 154(b) by 522 days.

(21) Appl. No.: 10/389,130

(22) Filed: Mar. 14, 2003

(65) Prior Publication Data

US 2004/0180346 A1  Sep. 16, 2004

(51) Int. Cl.
*C12P 19/34* (2006.01)
*C12M 1/34* (2006.01)

(52) U.S. Cl. .................... 435/91.2; 435/287.2
(58) Field of Classification Search ............... 435/6, 435/91.2, 287.2
See application file for complete search history.

(56) References Cited

U.S. PATENT DOCUMENTS

| | | | |
|---|---|---|---|
| 5,422,277 A * | 6/1995 | Connelly et al. ............. | 436/10 |
| 6,521,427 B1 | 2/2003 | Evans | |
| 6,670,153 B1 * | 12/2003 | Stern ........................... | 435/91.2 |
| 6,767,706 B1 * | 7/2004 | Quake et al. ................. | 435/6 |
| 2002/0141903 A1 * | 10/2002 | Parunak et al. .............. | 422/101 |
| 2005/0042639 A1 * | 2/2005 | Knapp et al. ................. | 435/6 |
| 2005/0079510 A1 * | 4/2005 | Berka et al. .................. | 435/6 |

FOREIGN PATENT DOCUMENTS

WO  WO 02/081490 A2  10/2002

OTHER PUBLICATIONS

Nagai et al., Anal. Chem. 73, 1043-1047 (2001).*

* cited by examiner

*Primary Examiner*—Kenneth R. Horlick
(74) *Attorney, Agent, or Firm*—Eddie E. Scott; Alan H. Thompson

(57) ABSTRACT

A system for nucleic acid amplification of a sample comprises partitioning the sample into partitioned sections and performing PCR on the partitioned sections of the sample. Another embodiment of the invention provides a system for nucleic acid amplification and detection of a sample comprising partitioning the sample into partitioned sections, performing PCR on the partitioned sections of the sample, and detecting and analyzing the partitioned sections of the sample.

10 Claims, 3 Drawing Sheets

CHEMICAL AMPLIFICATION BASED ON FLUID PARTITIONING

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to chemical amplification and more particularly to chemical amplification based on fluid partitioning.

2. State of Technology

U.S. Pat. No. 4,683,202 issued Jul. 28, 1987; U.S. Pat. No. 4,683,195 issued Jul. 28, 1987; and U.S. Pat. No. 4,800,159 issued Jan. 24, 1989 to Kary B. Mullis et al provide background information. The patents describe processes for producing any particular nucleic acid sequence from a given sequence of DNA or RNA in amounts which are large compared to the amount initially present. The DNA or RNA may be single-or-double-stranded, and may be a relatively pure species or a component of a mixture of nucleic acids. The process utilizes a repetitive reaction to accomplish the amplification of the desired nucleic acid sequence. The extension product of one primer when hybridized to the other becomes a template for the production of the desired specific nucleic acid sequence, and vice versa, and the process is repeated as often as is necessary to produce the desired amount of the sequence.

U.S. Pat. No. 6,503,715 for a nucleic acid ligand diagnostic biochip issued Jan. 7, 2003 provides the following background information, "Methods are provided in the instant invention for obtaining diagnostic and prognostic Nucleic acid ligands, attaching said ligands to a Biochip, and detecting binding of target molecules in a Bodily to said Biochip-bound Nucleic acid ligands." In one embodiment of the instant invention, one or more Nucleic acid ligands are chosen that bind to molecules known to be diagnostic or prognostic of a disease; these ligands are then attached to the Biochip. Particular methods for attaching the Nucleic acid ligands to the Biochip are described below in the section entitled "Fabrication of the Nucleic Acid Biochip." The Biochip may comprise either (i) Nucleic acid ligands selected against a single target molecule; or more preferably, (ii) Nucleic acid ligands selected against multiple target molecules.

U.S. Patent Application No. 2002/0197623 for nucleic acid detection assays published Dec. 26, 2002 provides the following background information, "means for the detection and characterization of nucleic acid sequences, as well as variations in nucleic acid sequences . . . methods for forming a nucleic acid cleavage structure on a target sequence and cleaving the nucleic acid cleavage structure in a site-specific manner. The structure-specific nuclease activity of a variety of enzymes is used to cleave the target-dependent cleavage structure, thereby indicating the presence of specific nucleic acid sequences or specific variations thereof."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an apparatus for nucleic acid amplification of a sample comprising means for partitioning the sample into partitioned sections and means for performing PCR on the partitioned sections of the sample. Another embodiment of the invention provides an apparatus for nucleic acid amplification and detection of a sample comprising means for partitioning the sample into partitioned sections, means for performing PCR on the partitioned sections of the sample, and means for detection and analysis of the partitioned sections of the sample. The present invention also provides a method of nucleic acid amplification of a sample comprising the steps of partitioning the sample into partitioned sections and subjecting the partitioned sections of the sample to PCR. Another embodiment of a method of the present invention provides a method of nucleic acid amplification and detection of a sample comprising the steps of partitioning the sample into partitioned sections, subjecting the partitioned sections of the sample to PCR, and detecting and analyzing the partitioned sections of the sample.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
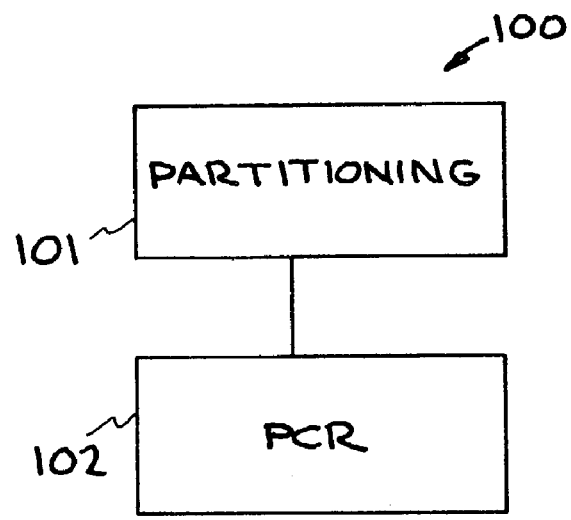
FIG. 1 is a flow diagram illustrating one embodiment of a system constructed in accordance with the present invention.

Referring now to the drawings, to the following detailed description, and to incorporated materials; detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings, and in particular to FIG. 1, a flow diagram of one embodiment of a system constructed in accordance with the present invention is illustrated. The system is designated generally by the reference numeral 100. The system 100 provides a method and apparatus for performing extremely rapid nucleic acid amplification. The flow diagram illustrating system 100 shows block 101 "partitioning" the sample and block 102 performing "CR" on the sample. The system 100 provides an apparatus for nucleic acid amplification of a sample comprising means for partitioning the sample and means for performing PCR on the sample. The system 100 also provides a method of nucleic acid amplification of a sample comprising the steps of partitioning the sample and subjecting the sample to PCR. The system 100 has application wherever current PCR-type systems exist.

In block 101 a chemical reagent and an input sample are "partitioned" into a large number of microdroplets or other forms of fluid partitions prior to amplification in block 102. The partitioning 101 involves dispersing the DNA-containing solution. For example the partitioning 101 can be accomplished by dispersing the DNA-containing solution in an immiscible carrier liquid. The DNA-containing solution is dispersed in the immiscible carrier fluid as microdroplets. The DNA-containing solution can be partitioned in other ways, for example, by being dispersed as liquid slugs separated by the carrier fluid, as an emulsion with the carrier fluid, or by using a gelling agent that prevents transfer of DNA between partitioned regions. The DNA-containing solution can also be partitioned mechanically by partitioning the fluid into micro-tubes or capillaries, or into micro-wells.

With the system 100, each partitioned DNA-containing fluid volume contains the necessary biochemical constituents for selectively amplifying a specified portion of a sample DNA via polymerase chain reaction (PCR). The target DNA can be detected by monitoring for the colorimetric indicator (e.g., flourescence or optical absorption) generated with each DNA template duplicaton sequence.

In block 102 selected portions of each nucleic acid sample are amplified using polymerase chain reaction (PCR), with the product contained in each partitioned fluid volume. This results in much more concentrated amplification product, since the volume containing the reaction is so small.

The polymerase chain reaction (PCR), is a cyclic process whereby a large quantity of identical DNA strands can be produced from one original template. The procedure was developed in 1985 by Kerry Mullis, who was awarded the 1993 Nobel prize in chemistry for his work. In PCR, DNA is immersed in a solution containing the enzyme DNA polymerase, unattached nucleotide bases, and primers, which are short sequences of nucleotides designed to bind with an end of the desired DNA segment. Two primers are used in the process: one primer binds at one end of the desired segment on one of the two paired DNA strands, and the other primer binds at the opposite end on the other strand. The solution is heated to break the bonds between the strands of the DNA, then when the solution cools, the primers bind to the separated strands, and DNA polymerase quickly builds a new strand by joining the free nucleotide bases to the primers in the 5'-3' direction. When this process is repeated, a strand that was formed with one primer binds to the other primer, resulting in a new strand that is restricted solely to the desired segment. Thus the region of DNA between the primers is selectively replicated. Further repetitions of the process can produce a geometric increase in the number of copies, (theoretically 2n if 100% efficient whereby n equals the number of cycles), in effect billions of copies of a small piece of DNA can be replicated in several hours.

A PCR reaction is comprised of (a) a double-stranded DNA molecule, which is the "template" that contains the sequence to be amplified, (b) primer(s), which is a single-stranded DNA molecule that can anneal (bind) to a complimentary DNA sequence in the template DNA; (c) dNTPs, which is a mixture of dATP, dTTP, dGTP, and dCTP which are the nucleotide subunits that will be put together to form new DNA molecules in the PCR amplification procedure; and (d) Taq DNA polymerase, the enzyme which synthesizes the new DNA molecules using dNTPs.

Current amplification systems are limited in practice to half hour type amplification and detection windows (~30 cycles, 1 minute/cycle). The system 100 provides faster amplification. This has many applications, for example, in Homeland Defense applications, faster detection methods (a few minutes) can push the deployment of these sensors from "detect to treat" to "detect to protect," having a serious impact on the number of casualties from a massive bioagent release.

The system 100 has significant advantages over typical bulk DNA detection techniques (even microscale bulk solution approaches), including (1) much faster detection time through a reduction in the total number of temperature cycles required, (2) a reduction in the time for each cycle, and (3) removing interference from competing DNA templates. The system 100 achieves a reduction in the total number of cycles by limiting the dilution of the optically generated signal (e.g., fluorescence or absorption). The formation of partitioned fluid volumes of the DNA-containing solution effectively isolates the fluid volumes which contain the target DNA from the fluid volumes that do not contain the target DNA. Therefore, the dilution of the optical signal is largely eliminated, allowing much earlier detection. This effect is directly related to the number of fluid partitions formed from the initial sample/reagent pool.

The system 100 achieves a reduction in the total number of cycles that are needed by limiting the dilution of the optically generated signal (e.g., fluorescence or absorption). The formation of partitioned fluid volumes of the DNA-containing solution effectively isolates the fluid volumes which contain the target DNA from the fluid volumes that do not contain the target DNA. Therefore, the dilution of the optical signal is largely eliminated, allowing much earlier detection. This effect is directly related to the number of fluid partitions formed from the initial sample/reagent pool. The effect of the number of fluid partitions on the number of cycles required for detection can be described by the following Equation E1:

$$N = \frac{\ln\left[D_L A_N\left(\frac{V}{X}\right)\right]}{\ln(2)}$$

where: N=number of cycles; $D_L$,=detection limit for optical signal [moles/liter]; X=initial number of DNA molecules; V=volume containing DNA molecules [liters]; $A_N$=Avagadro's number [6.023×1023 molecules/mole]. From Equation E1 it is clear that N, the number of cycles until detection, decreases as V, the partitioned fluid volume, decreases.

The system 100 reduces the duration of each temperature cycle by effectively increasing the concentration of reactants by enclosing them in picoliter type volumes. Since reaction rates depend on the concentration of the reactants, the efficiency of a partitioned fluid volume or droplet should be higher than in an ordinary vessel (such as a test tube) where the reactant quantity (DNA quantity) is extremely low. It is estimated that through the reduction in the number of cycles and the reduction in the time required for each cycles that the FPDD technique can reduce the detection time by an order of magnitude as compared to bulk solution DNA detection techniques.

The system 100 facilitates removal of interference from competing DNA templates. Given the extremely small volumes involved with Fluid-Partitioned DNA Detection (FPDD), it is possible to isolate a single template of the target DNA in a given partitioned volume or microdroplet. For example, the formation of 2000 partitioned fluid volumes or microdroplets (each with a volume of $5 \times 10^{-9}$ liters) made by dividing a bulk solution of 10 microliters containing 200 DNA molecules, would result in one DNA molecule per microdroplet on average. This makes it possible to amplify only one template in mixtures containing many kinds of templates without interference. This is extremely important in processing of real world aerosol samples containing complex mixtures of DNA from many sources, and has direct application in screening of cDNA libraries.

Figure 2:
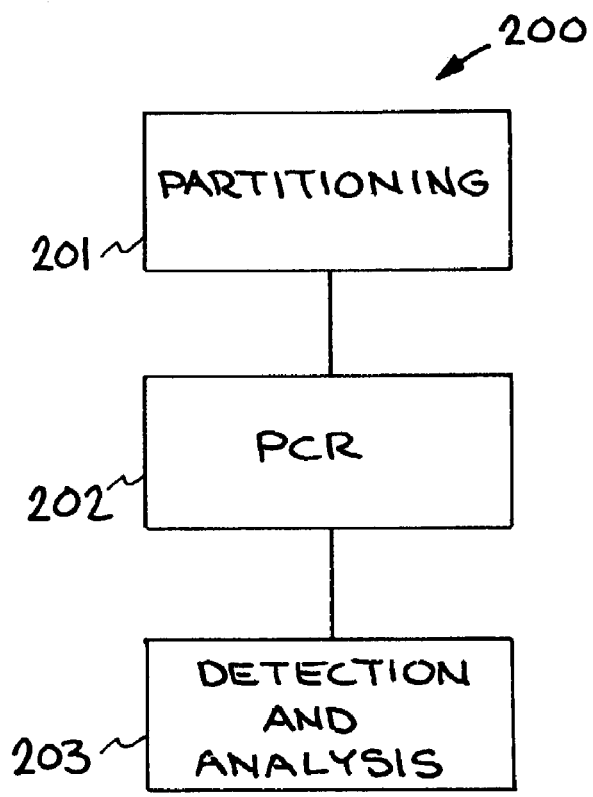
FIG. 2 is a flow diagram illustrating another embodiment of a system constructed in accordance with the present invention.

Referring now to FIG. 2, a flow diagram of another embodiment of a system constructed in accordance with the present invention is illustrated. The system is designated generally by the reference numeral 200. The flow diagram illustrating system 200 shows block 201 "partitioning" the sample, block 202 performing "PCR" on the sample, and block 203 "detection and analysis." The system 200 provides a method and apparatus for performing extremely rapid nucleic acid amplification and detection. The system 200 provides an apparatus for nucleic acid amplification of a sample comprising means for partitioning the sample into partitioned sections, means for performing PCR on the partitioned sections, and means for detection and analysis of the partitioned sections. The system 200 also provides a method of nucleic acid amplification of a sample comprising the steps of partitioning the sample into partitioned sections, subjecting the partitioned sections to PCR, and detecting and analyzing the partitioned sections of the sample.

In block 201 a chemical reagent and an input sample are "partitioned" into a large number of microdroplets or other forms of fluid partitions prior to amplification. The system 200 achieves a reduction in the total number of cycles by limiting the dilution of the optically generated signal (e.g., fluorescence or absorption). The formation of partitioned fluid volumes of the DNA-containing solution effectively isolates the fluid volumes which contain the target DNA from the fluid volumes that do not contain the target DNA. Therefore, the dilution of the optical signal is largely eliminated, allowing much earlier detection. This effect is directly related to the number of fluid partitions formed from the initial sample/reagent pool.

In block 202 selected portions of each nucleic acid sample are then amplified using polymerase chain reaction (PCR), with the product contained in each partitioned fluid volume. This results in much more concentrated amplification product, since the volume containing the reaction is so small. If a Taqman type detection approach is used, fluorescent dye molecules unquenched by the PCF amplification are also more concentrated, making possible earlier optical based detection. Since it is possible to contain very amounts of the starting target DNA in each partition fluid volume, inhibitory competition from near-neighbor DNA templates is less allowing screening of very dilute samples.

In block 203 partitioned portions of the sample are detected by monitoring for the calorimetric indicator (e.g., fluorescence or optical absorption) generated with each DNA template duplication sequence. The partitioned portions of the sample are optically probed to detect the colorimetric indicator which signals the presence of the target DNA. The partitioned portions of the sample can also be scanned optically to detect the colorimetric indicator signaling the presence of the target DNA. In one embodiment, fluorescence, generated by degradation of the dye/quencher pair on the primer, is detected using a confocal imaging system such as that employed in conventional flow cytometers. Scattering profiles from individual microdroplets, as in conventional flow cytometers, can be used to eliminate background signal from other particles.

The system 200 has application wherever current PCR-type systems exist, including medical, drug-discovery, biowarfare detection, and other related fields. Biowarfare detection applications include identifying, detecting, and monitoring bio-threat agents that contain nucleic acid signatures, such as spores, bacteria, etc. Biomedical applications include tracking, identifying, and monitoring outbreaks of infectious disease. The system 200 provides rapid, high throughput detection of biological pathogens (viruses, bacteria, DNA in biological fluids, blood, saliva, etc.) for medical applications. Forensic applications include rapid, high throughput detection of DNA in biological fluids for forensic purposes. Food and beverage safety applications include automated food testing for bacterial contamination.

Figure 3:
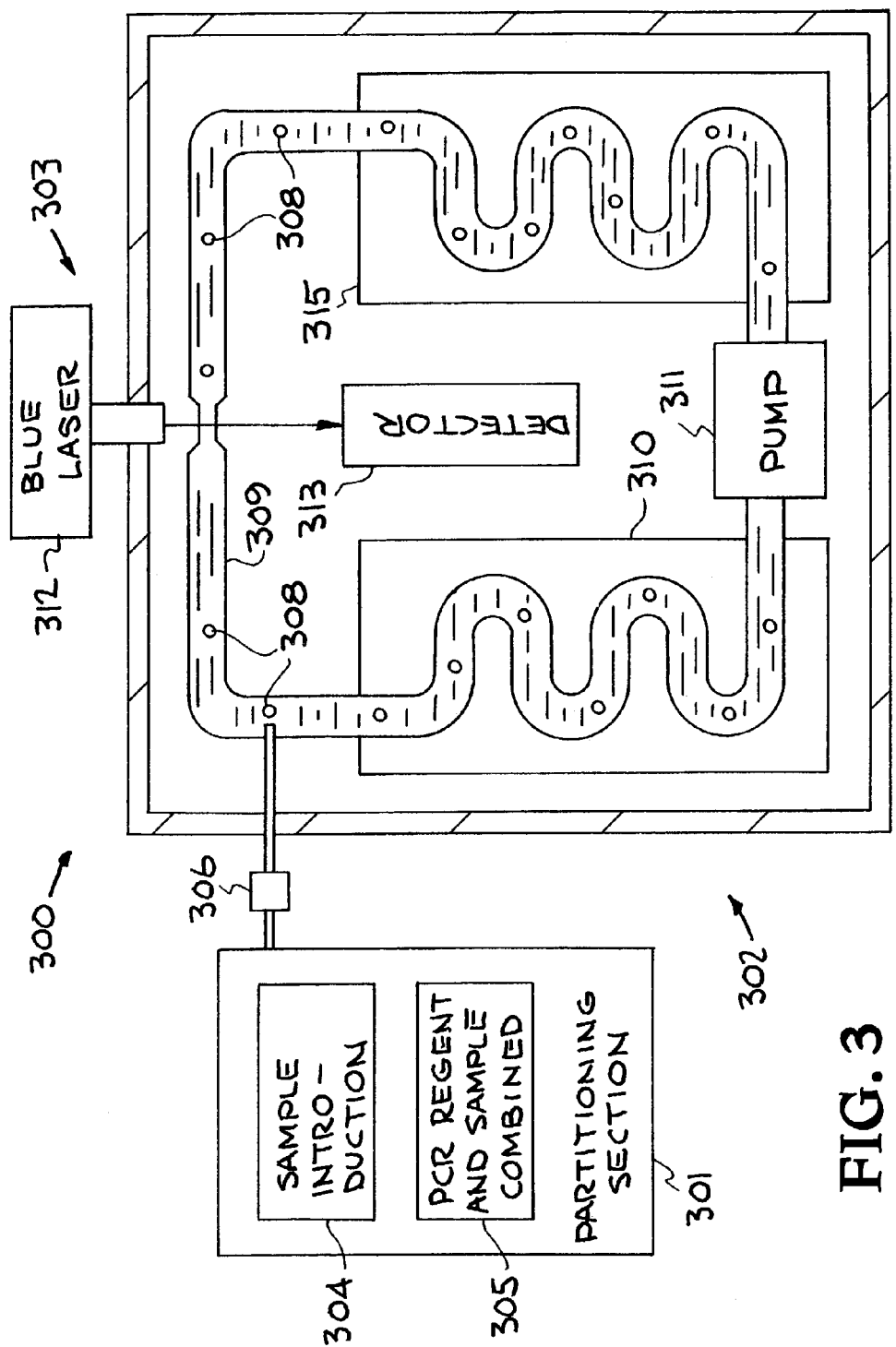
FIG. 3 is a diagram of another embodiment of a system constructed in accordance with the present invention.

Referring now to FIG. 3, a diagram of another embodiment of a system constructed in accordance with the present invention is illustrated. The system is designated generally by the reference numeral 300. The system 300 provides an instrument for performing Fluid-Partitioned DNA Detection (FPDD) with PCR based detection and amplification. The system 300 includes a partitioning section 301, a PCR section 302, and a detection and analysis section 303.

The partitioning section 301 includes a sample introduction unit 304 and a unit 305 where the sample and a PCR reagent are combined. The sample and a PCR reagent are injected through a small orifice 306. The injection of the sample through the small orifice 306 produces microdroplets 308.

The PCR section 302 includes a continuous tube 309 for circulating the microdroplets 308 and suspended in an immiscible carrier fluid 314. The microdroplets 308 suspended in an immiscible carrier fluid 314 are pumped through the continuous tube 309 by pump 311. The microdroplets 308 suspended in an immiscible carrier fluid 314 are cycled through heater 310 and cooler 315 to perform PCR.

The detection and analysis section 303 includes a blue laser 312 and a detector 313. The laser 312 is projected upon the droplets 308 as they pass through tube 308 between the laser 312 and the detector 313.

In the system 300, the DNA-containing solution is partitioned into many microdroplets 308 and suspended in an immiscible carrier fluid 314. The microdroplets 308 are formed by forcing the PCR mix (sample and reagent) through the small orifice or microjet 306. These microdroplets 308 are then captured in the immiscible fluid 314, such as mineral oil, and flowed past the heating element 310 and cooler 315. An optical signal (e.g., fluorescence or optical absorption), generated by degradation of the dye/quencher pair on the primer, is detected using a confocal imaging system such as that employed in conventional flow cytometers. Scattering profiles from individual microdroplets, as in conventional flow cytometers, can be used to eliminate background signal from other particles. Once exposed to multiple heating cycles, the microdroplets can be identified and probed for an optical signal at rates of several thousand per second.

The FPDD system achieves a reduction in the total number of cycles by limiting the dilution of the optically generated signal (e.g., fluorescence or absorption). The formation of partitioned fluid volumes of the DNA-containing solution effectively isolates the fluid volumes which contain the target DNA from the fluid volumes that do not contain the target DNA. Therefore, the dilution of the optical signal is largely eliminated, allowing much earlier detection. This effect is directly related to the number of fluid partitions formed from the initial sample/reagent pool. The effect of the number of fluid partitions on the number of cycles required for detection is described by the Equation E1 set out earlier.

The FPDD technique reduces the duration of each temperature cycle by effectively increasing the concentration of reactants by enclosing them in picoliter type volumes. Since reaction rates depend on the concentration of the reactants, the efficiency of a partitioned fluid volume or droplet should be higher than in an ordinary vessel (such as a test tube) where the reactant quantity (DNA quantity) is extremely low. It is estimated that through the reduction in the number of cycles and the reduction in the time required for each cycles that the FPDD technique can reduce the detection time by an order of magnitude as compared to bulk solution DNA detection techniques The FPDD technique facilitates removal of interference from competing DNA templates. Given the extremely small volumes involved with FPDD, it is possible to isolate a single template of the target DNA in a given partitioned volume or microdroplet. For example, the formation of 2000 partitioned fluid volumes or microdroplets (each with a volume of $5 \times 10^{-9}$ liters) made by dividing a bulk solution of 10 microliters containing 200 DNA molecules, would result in one DNA molecule per microdroplet on average. This makes it possible to amplify only one template in mixtures containing many kinds of templates without interference. This is extremely important in processing of real world aerosol samples containing complex mixtures of DNA from many sources, and has direct application in screening of cDNA libraries.

With this new bioassay technique, each partitioned DNA-containing fluid volume contains the necessary biochemical constituents for selectively amplifying a specified portion of a sample DNA via polymerase chain reaction (PCR). The target DNA is detected by monitoring for the colorimetric indicator (e.g., fluorescence or optical absorption) generated with each DNA template duplication sequence.

The system 300 provides a fast, flexible and inexpensive high throughput, bioassay technology based on creation and suspension of microdroplets in an immiscible carrier stream. Each microdroplet contains the necessary biochemical constituents for selectively amplifying and fluorescently detecting a specified portion of a sample DNA via polymerase chain reaction (PCR). Once exposed to multiple heating cooling cycles, the microdroplets can be identified and probed for fluorescent signal at rates of several thousand per second.

Isolating the PCR reaction in such small (picoliter) volumes provides an order of magnitude reduction in overall detection time by:

(1) reducing the duration of each temperature cycle—the concentration of reactants increases by enclosing them in picoliter type volumes. Since reaction kinetics depend on the concentration of the reactant, the efficiency of a microdroplet should be higher than in an ordinary vessel (such a test tube) where the reactant quantity is infinitesimal (2) reducing the total number of cycles—dilution of the fluorescently generated signal is largely eliminated in such a small volume, allowing much earlier detection. This effect is directly related to the number of microdroplets formed from the initial sample/reagent pool. Since PCR is an exponential process, for example, 1000 microdroplets would produce a signal 10 cycles faster than typical processing with bulk solutions.

(3) removing interference from competing DNA templates—given the extremely small volumes involved, it is possible to isolate a single template of the target DNA in a given microdroplet. A pL microdoplet filled with a 1 pM solution, for example, will be occupied by only one molecule on average. This makes it possible to amplify only one template in mixtures containing many kinds of templates without interference. This is extremely important in processing of real world aerosol samples containing complex mixtures of DNA from many sources, and has direct application in screening of precious cDNA libraries.

Figure 4:
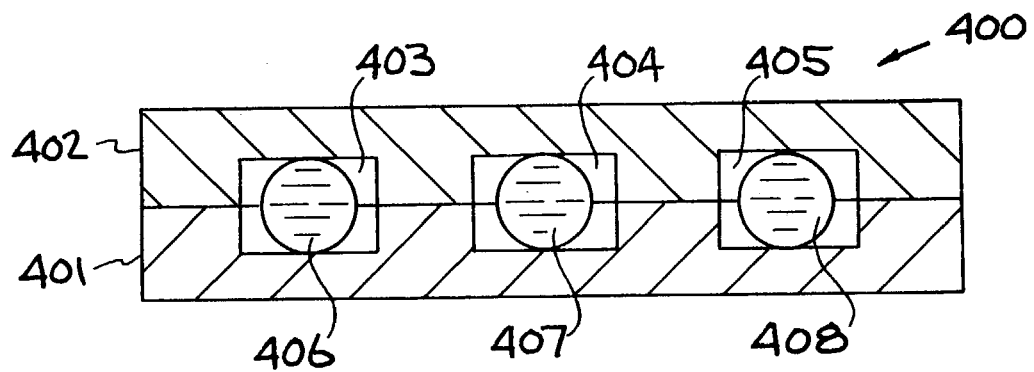
FIG. 4 is a diagram of another embodiment of a system constructed in accordance with the present invention.

Referring now to FIG. 4, an illustration of another embodiment of a system constructed in accordance with the present invention is illustrated. The system is designated generally by the reference numeral 400. The system 300 provides system for nucleic acid amplification of a sample. The system 400 includes means for partitioning the sample into partitioned sections and means for performing PCR on the partitioned sections of the sample.

The sample is separated into immiscible slugs 406, 407, and 408. The immiscible slugs 406, 407, and 408 are formed through a system of microfluidics. Background information on microfluidics is contained in U.S. Pat. No. 5,876,187 for micropumps with fixed valves to Fred K. Forster et al., patented Mar. 2, 1999. As stated in U.S. Pat. No. 5,876,187, "Miniature pumps, hereafter referred to as micropumps, can be constructed using fabrication techniques adapted from those applied to integrated circuits. Such fabrication techniques are often referred to as micromachining. Micropumps are in great demand for environmental, biomedical, medical, biotechnical, printing, analytical instrumentation, and miniature cooling applications." Microchannels 403, 404, and 405 are formed in substrates 401 and 402. The disclosures of U.S. Pat. Nos. 5,876,187 and 5,876,187 are incorporated herein by reference.

The immiscible slugs 406, 407, and 408 can be moved through the microchannels using magnetohydrodynamics. Background information on magnetohydrodynamics is contained in U.S. Pat. No. 6,146,103 for micromachined magnetohydrodynamic actuators and sensors to Abraham P. Lee and Asuncion V. Lemoff, patented Nov. 14, 2000. As stated in U.S. Pat. No. 6,146,103, "Microfluidics is the field for manipulating fluid samples and reagents in minute quantities, such as in micromachined channels, to enable hand-held bioinstrumentation and diagnostic tools with quicker process speeds. The ultimate goal is to integrate pumping, valving, mixing, reaction, and detection on a chip for biotechnological, chemical, environmental, and health care applications. Most micropumps developed thus far have been complicated, both in fabrication and design, and often are difficult to reduce in size, negating many integrated fluidic applications. Most pumps have a moving component to indirectly pump the fluid, generating pulsatile flow instead of continuous flow. With moving parts involved, dead volume is often a serious problem, causing crosscontamination in biological sensitive processes. The present invention utilizes MHDs for microfluid propulsion and fluid sensing, the microfabrication methods for such a pump, and the integration of multiple pumps for a microfluidic system. MHDs is the application of Lorentz force law on fluids to propel or pump fluids. Under the Lorentz force law, charged particles moving in a uniform magnetic field feel a force perpendicular to both the motion and the magnetic field. It has thus been recognized that in the microscale, the MHD forces are substantial for propulsion of fluids through microchannels as actuators, such as a micropump, micromixer, or microvalve, or as sensors, such as a microflow meter, or viscosity meter. This advantageous scaling phenomenon also lends itself to micromachining by integrating microchannels with micro-electrodes." The disclosure of U.S. Pat. No. 6,146,103 is incorporated herein by reference.

The means for performing PCR on the partitioned sections of the sample can be a system for alternately heating and cooling the immiscible slugs 406, 407, and 408. Alternatively, the means for performing PCR on the partitioned sections of the sample can be a system for alternately heating and cooling the immiscible slugs 406, 407, and 408 can be a system for moving the immiscible slugs 406, 407, and 408 through zones for heating and cooling. An example of such a system is shown in U.S. patent application No. 2002/0127152 published Sep. 12, 2002 for a convectively driven PCR thermal-cycling system described as follows: "A polymerase chain reaction system provides an upper temperature zone and a lower temperature zone in a fluid sample. Channels set up convection cells in the fluid sample and move the fluid sample repeatedly through the upper and lower temperature zone creating thermal cycling." The disclosure of U.S. Patent Application No. 2002/0127152 is incorporated herein by reference.

In another embodiment of the invention, the DNA-containing solution is partitioned by adding a gelling agent to the solution to form cells of partitioned volumes of fluid separated by the gelling agent. Using this approach for fluid partitioning, the DNA-containing solution is gelled in a tube or as a very thin layer. For example, it can be in a thin layer between flat plates and the surface of the thin film can be optically probed spatially in directions parallel to the film surface to detect micro-regions in the film where the colorimetric indicator suggests the presence of the target DNA.

Another embodiment of the invention is to partition the DNA-containing solution as microdroplets in an immiscible fluid where the droplets are arranged in a two-dimensional array such that the array of microdroplets can be optically probed to detect the colorimetric indicator which signals the presence of the target DNA. In this approach a solid hydrophobic substrate supports the microdroplets. For example, in small indentations, and the immiscible "partitioning" fluid is less dense than the aqueous DNA-containing solution.

In another embodiment of the invention the DNA-containing solution is partitioned using mechanical means. For example, the DNA-containing solution can be partitioned into an array of capillaries, microtubes, or wells. In this approach, the micro vessels holding each partitioned fluid volume can be scanned optically to detect the colorimetric indicator signaling the presence of the target DNA.

Figure 5A:
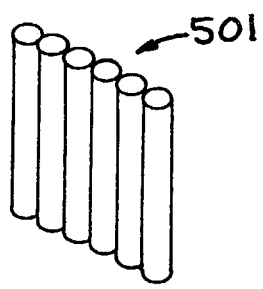
FIG. 5 is a diagram of another embodiment of a system constructed in accordance with the present invention.
Figure 5B:
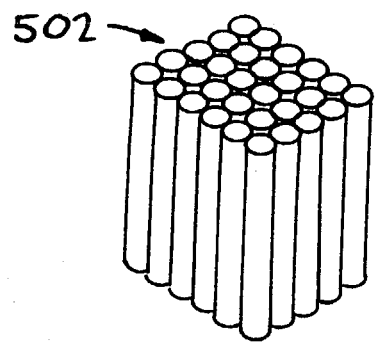
Figure 5C:
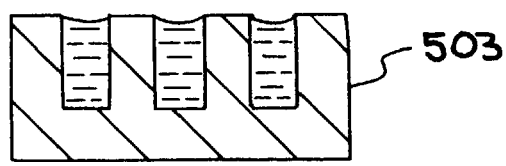

Referring now to FIGS. 5A, 5B, and 5C example representations of the mechanical partitioning approach for DNA detection using fluid partitioning are shown. In FIG. 5A a line of capillaries or micro-tubes 501 are used for partitioning and holding the DNA containing solution. In FIG. 5B an array 502 of capillaries or micro-tubes are used for partitioning the DNA-containing solution. In FIG. 5C a micro-wells or micro-vessels unit 503 is used for partitioning and holding the DNA-containing solution.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for nucleic acid amplification of a sample, comprising:
    means for partitioning said sample into partitioned sections, wherein said means for partitioning said sample into partitioned sections comprises an injection orifice, and
    means for performing PCR on said partitioned sections of said sample.

2. The apparatus for nucleic acid amplification of a sample of claim 1 wherein said injection orifice is an injection orifice that produces microdroplets.

3. The apparatus for nucleic acid amplification of a sample of claim 1 wherein said injection orifice is an injection orifice that injects said sample and a PCR reagent.

4. The apparatus for nucleic acid amplification of a sample of claim 1 wherein said means for performing PCR on said partitioned sections of said sample comprises a continuous tube for circulating said partitioned sections of said sample through a heater to perform PCR.

5. The apparatus for nucleic acid amplification of a sample of claim 1 wherein said means for performing PCR on said partitioned sections of said sample comprises a continuous tube for circulating said partitioned sections of said sample through a heater and cooler to perform PCR.

6. The apparatus for nucleic acid amplification of a sample of claim 1 wherein said means for performing PCR on said partitioned sections of said sample comprises a pump, a continuous tube, and a heater.

7. The apparatus for nucleic acid amplification of a sample of claim 1 including means for detection and analysis of said partitioned sections of said sample comprising a laser and a detector.

8. The apparatus for nucleic acid amplification of a sample of claim 1 including means for detection and analysis of said partitioned sections of said sample comprising a blue laser and a detector.

9. The apparatus for nucleic acid amplification of a sample of claim 1 wherein said means for partitioning said sample into partitioned sections comprises means for separating said sample into immiscible slugs.

10. A method of nucleic acid amplification of a sample, comprising the steps of:
    partitioning said sample into partitioned sections, wherein said step of partitioning said sample into partitioned sections comprises flowing said sample through an injection orifice, and
    subjecting said partitioned sections of said sample to PCR.

* * * * *